(12) United States Patent
Bohn

(10) Patent No.: US 6,707,877 B2
(45) Date of Patent: Mar. 16, 2004

(54) POSITIONING MECHANISM PROVIDING PRECISION 2-AXIS ROTATION, 1-AXIS TRANSLATION ADJUSTMENT

(75) Inventor: David D Bohn, Ft Collins, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 339 days.

(21) Appl. No.: 09/966,905

(22) Filed: Sep. 27, 2001

(65) Prior Publication Data

US 2003/0058993 A1 Mar. 27, 2003

(51) Int. Cl.[7] .......................... G01N 23/083; B23Q 1/25

(52) U.S. Cl. .............................. 378/21; 378/25; 269/55; 269/903

(58) Field of Search .............................. 378/20, 21, 22, 378/25; 269/55, 903

Primary Examiner—David V Bruce
(74) Attorney, Agent, or Firm—Kyle J. Way

(57) ABSTRACT

A mechanism for adjusting an object in terms of its position along a vertical axis, and its rotational orientation about either two orthogonal horizontal axes or about a vertical and a horizontal axis, utilizes a set of electric motors in conjunction with a mechanical guiding structure that substantially restricts the movement of the object to the desired translational and rotational directions.

51 Claims, 13 Drawing Sheets

POSITIONING MECHANISM PROVIDING PRECISION 2-AXIS ROTATION, 1-AXIS TRANSLATION ADJUSTMENT

BACKGROUND OF THE INVENTION

Today, image-based inspection systems are often employed for physical inspection of an object of interest. Such systems typically employ an optical- or x-ray-based source at a distance from an object of interest at which an area of the object is in focus. Additionally, many such systems currently employ a positioning mechanism whereby the distance between the imaging source and the object is adjustable so that the surface to be inspected may be brought into proper focus.

For example, x-ray laminography machines that are employed to inspect printed circuit boards (PCBs) for manufacturing defects often utilize such a mechanism to keep a small portion of the board under inspection near a focal plane. The position of the focal plane is determined by the location of an x-ray source and x-ray detector, which reside on opposite sides of the PCB under inspection. The area under inspection, which is roughly square in shape, is typically much smaller than the area of the PCB itself, and commonly on the order of one-quarter- to one-inch across.

Unfortunately, warping of the PCB may be of sufficient severity that some portion of the area being inspected may remain out of focus, forcing the use of an even smaller inspection area. As seen in FIG. 1, a warped PCB 100 may cause all but a small area on the top side of PCB 100 to reside outside of a depth of focus 110 of an optical or x-ray inspection system, resulting in a small area, defined by a narrow width 120, that may be inspected at any one time. The use of a reduced inspection area generally results in more inspection areas being necessary for each PCB, thereby resulting in a significantly longer inspection time required for each PCB and, consequently, a drastic reduction in PCB inspection throughput.

Additionally, the focus problems due to PCB warping can also cause the inspection system to falsely identify out-of-focus areas of the PCB under inspection as manufacturing defects, resulting in costs due to unnecessary additional testing or discarding of properly manufactured PCBs.

Such problems regarding a changing focal distance over the surface of an object is not limited to PCB x-ray laminography inspection machines. Other optical or x-ray-based viewing or inspection machines that employ only a focal length adjustment likely encounter the same difficulties with objects having a nonplanar structure to be viewed or inspected.

Therefore, from the foregoing, a new positioning adjustment mechanism that allows more area of an object under inspection to reside within the depth of focus, thus allowing for a greater inspection area and, thus, higher inspection throughput, would be advantageous.

SUMMARY OF THE INVENTION

Embodiments of the invention, to be discussed in detail below, allow an object under inspection to be rotated and translated in such a manner that more of the object will reside within the depth of focus of an image-based inspection machine. Continuing with the PCB example in FIG. 2, if the warped PCB 100 (from FIG. 1) is rotated about an axis within the plane generally defined by depth of focus 110, more area of the top surface of PCB 100, as defined by larger width 200, lies within depth of focus 110. Since warping or other irregularities in an object under inspection can occur in any direction along a surface of the object, the ability of an adjustment mechanism to rotate the object about any two orthogonal horizontal axes to account for any such irregularities is desirable.

Assuming that a focal plane of an inspection system is oriented horizontally, as shown in FIGS. 1 and 2, a mechanism according to an embodiment of the invention allows for both translation of an object under inspection along a vertical axis as well as rotational orientation of the object about two horizontal axes, each of which is orthogonal to the vertical axis and to each other. The mechanism includes, in part, means for retaining the object under inspection. That retaining means is then guided mechanically to pivot about the two horizontal axes as well as translate along the vertical axis. The retaining means is also prevented from horizontal translational movement, as well as rotational movement about the vertical axis. Means for translating at least three distinct areas of the retaining means along the vertical axis is also provided, with those three areas being positioned so that the retaining means may be rotated about the first and second horizontal axes by the translating means.

An adjustment mechanism according to another embodiment of the invention allows for translation of an object under inspection along a vertical axis as well as rotation of the object about both the vertical axis and a horizontal axis that is orthogonal to the vertical axis. The mechanism includes, in part, means for retaining the object, and means for rotating the retaining means about the vertical axis. Means for guiding the rotating means permits the rotating means to pivot only about the horizontal axis. The guiding means and the rotating means are coupled so that they are permitted to move translationally along the vertical axis. Means for translating at least two distinct areas of the rotating means along the vertical axis is also included, with the two areas residing on opposite sides of the horizontal axis.

Another embodiment of the invention exists in the form of a method for adjusting both the location of an object along a vertical axis and the rotational orientation of the object about a first and second horizontal axes, with the first and second horizontal axes each being orthogonal to the vertical axis and to each other. The object under inspection is allowed to pivot about the first and second horizontal axes, and to translate along the vertical axis, while being prevented from either substantial translational movement in the plane defined by the first and second horizontal axes or substantial rotational movement about the vertical axis. At least three areas of the object are then translated substantially along the vertical axis, with the three areas being positioned so that the object may also be rotated about the first and second horizontal axes so that the object resides in a predetermined vertical position and rotational orientation.

Another method embodiment adjusts both the location of an object along a vertical axis and the rotational orientation of the object about the vertical axis and a horizontal axis that is orthogonal to the vertical axis. The object is allowed to rotate about a vertical axis and pivot about the horizontal axis, while being restricted with respect to other translational and rotational movement. The object is then rotated about the vertical axis, pivoted about the horizontal axis, translated along the vertical axis until the object resides in a predetermined vertical position and rotational orientation.

Other aspects and advantages of the invention will become apparent from the following detailed description, taken in conjunction with the accompanying drawings, illustrating by way of example the principles of the invention.

DETAILED DESCRIPTION OF THE PREFERRED EMBODIMENTS

The embodiments of the invention, which are described below, are fashioned to adjust the position of a PCB within the environment of an x-ray laminography inspection system. However, other inspection systems, whether based on optics, x-ray, or other detection means, could utilize such a system advantageously.

In the following embodiments, the inspection system of interest is assumed to be oriented such that the image detection source is located above the positioning adjustment mechanism, and directed downward. While this arrangement is the most popular one employed in image-based inspection systems, other orientations of such systems and their associated positioning adjustment mechanisms are contemplated within the scope of the following embodiments.

Figure 1:
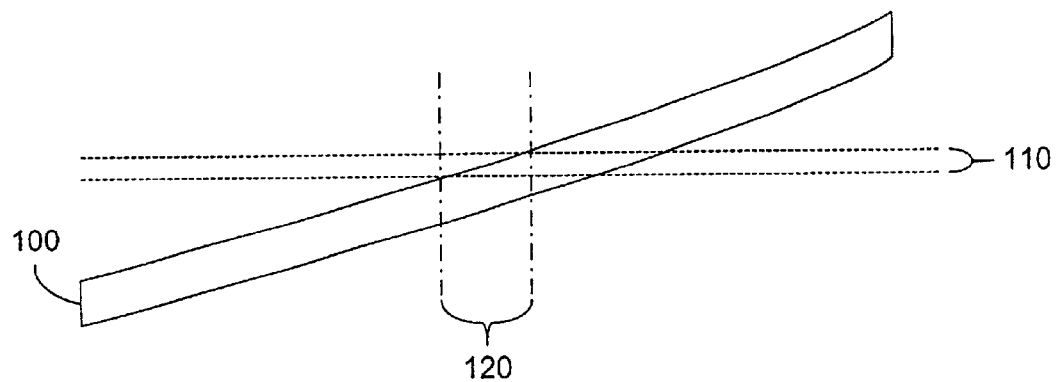
FIG. 1 is a diagram of a horizontally-oriented PCB that is warped to such an extent that the depth of focus associated with an image-based inspection system from the prior art covers allows only a small area of the PCB to be inspected at a time.
Figure 2:
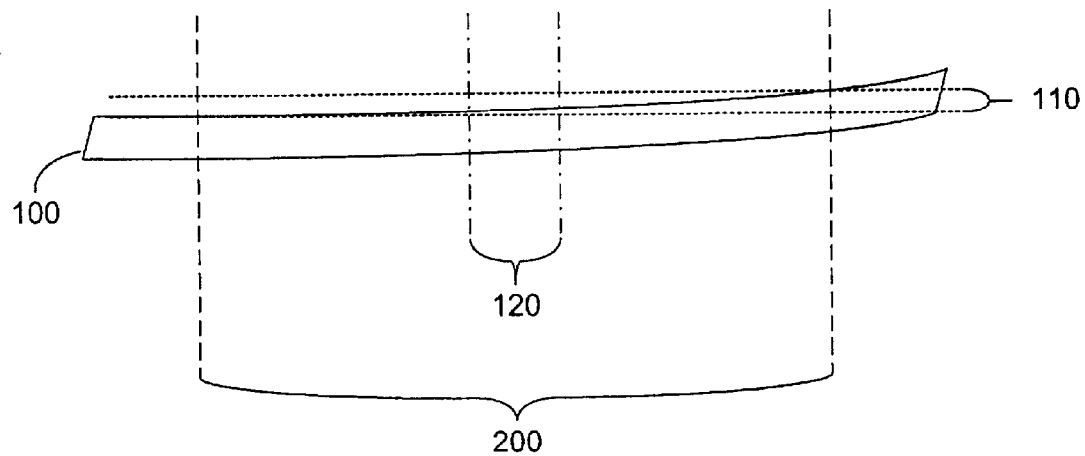
FIG. 2 is a diagram of the PCB from FIG. 1 that is rotated about a horizontal axis so that a larger area of the PCB may be inspected at one time by an image-based inspection system according to an embodiment of the invention.
Figure 3:
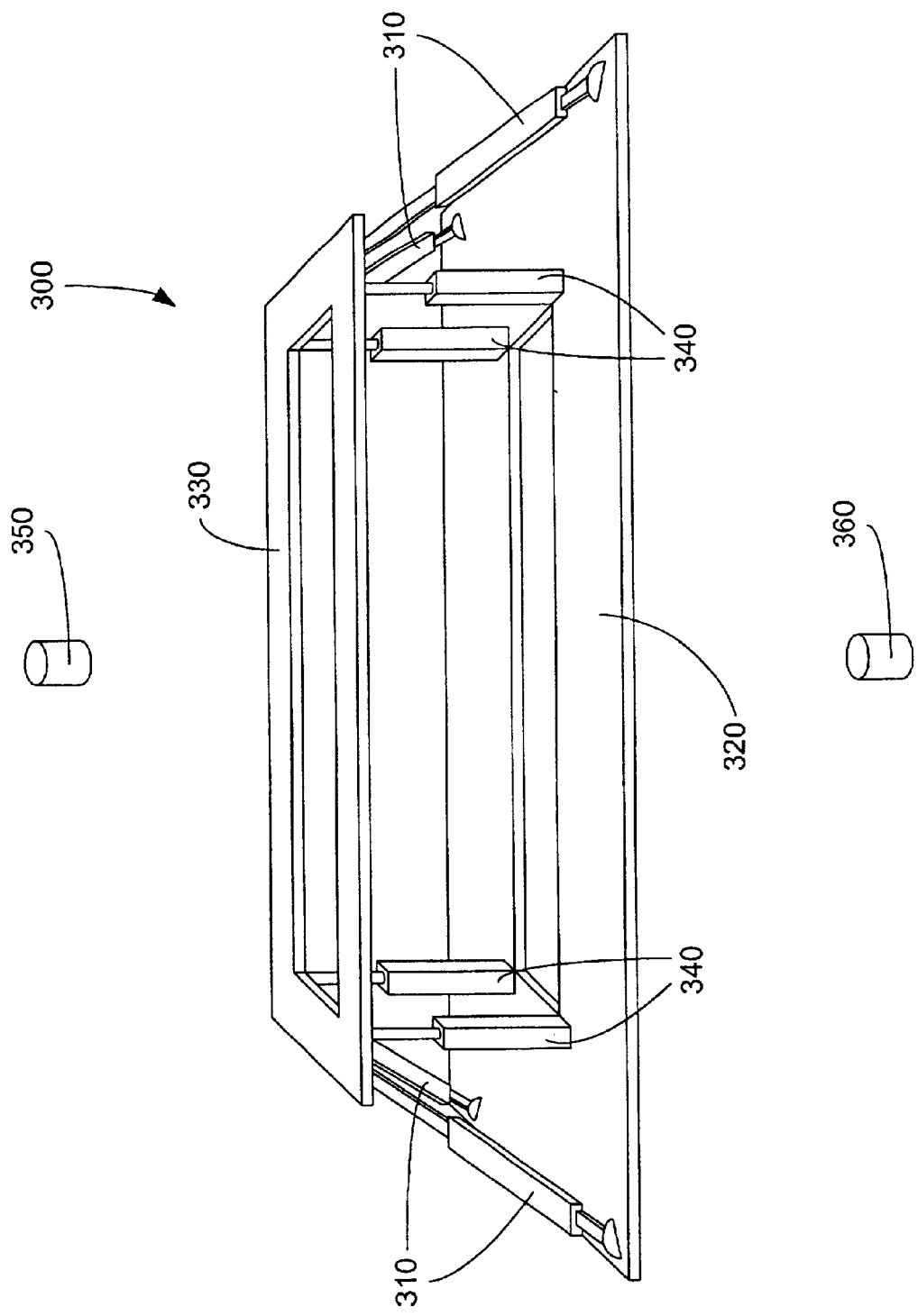
FIG. 3 is a perspective view of an adjustment mechanism according to an embodiment of the invention that utilizes struts to allow a PCB under inspection to translate vertically and rotate about two horizontal axes while restricting both horizontal translation and rotation about a vertical axis.

An adjustment mechanism 300 according to an embodiment of the invention is shown in FIG. 3. Four struts 310 are coupled at their lower ends to a stable base 320, and are coupled at their upper ends near the corners of a retaining plate 330, which holds the PCB to be inspected (not shown). Struts 310 are oriented downward and outward from retaining plate 330. Since three points are sufficient to define a plane, as few as three struts may be used in an alternative embodiment.

Stable base 320 may be a stationary plate. Alternately, stable base 320 may be a horizontal translation table that is capable of moving translationally within a horizontal plane according to the particular inspection system in which it is employed. Such translational movement allows the retained PCB to be inspected one small area at a time using a stationary x-ray laminography source.

Figure 4:
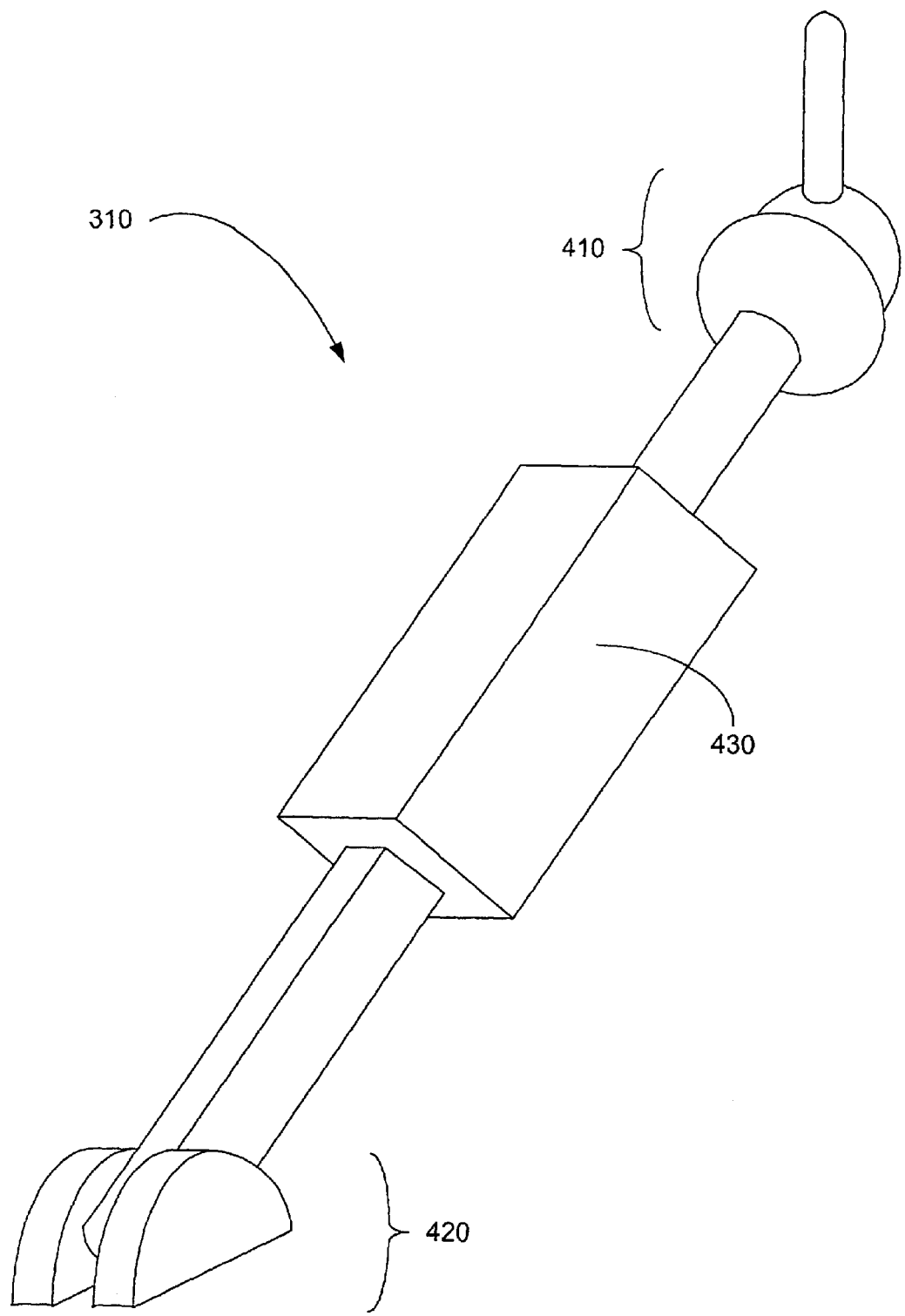
FIG. 4 is a perspective view of one of the struts utilized in the adjustment mechanism of FIG. 3.

FIG. 4 shows one possible version of strut 310. At the upper end of strut 310 resides a two-axis ball joint 410, and, at the lower end, a one-axis pivot joint 420. In between the two ends of strut 310 resides a translational dampener 430 that allows dampened translational movement along the longitudinal axis of strut 310. One-axis pivot joint 420 allows rotation only about the horizontal axis defined by that joint, while two-axis ball joint 410 allows rotation about that same axis, as well as the horizontal axis orthogonal to that axis. Two-axis ball joint 410 does not allow any appreciable movement about a vertical axis.

The collective orientation and action of struts 310 in adjustment mechanism 300 (FIG. 3), in conjunction with stable base 320, provide a motion guiding structure which allows retaining plate 330 to translate vertically as well as to rotate about any two orthogonal horizontal axes. The translational movement allows an area of a PCB under inspection to be brought into focus by bringing the PCB to the proper height within the depth of focus defined by an x-ray source 350 located above the PCB and an x-ray detector 360 located below. The positions of x-ray source 350 and x-ray detector 360 may also be reversed, depending on the application. The rotational movement allows the PCB to be oriented about two orthogonal horizontal axes so that the maximum area of the PCB will lie within the depth of focus.

Struts 310 also substantially limit horizontal translation and rotation about a vertical axis. Such limitations in movement are helpful in accurately controlling the movement of the PCB under inspection so that the area of the PCB to be inspected is readily located and identified by the inspection system.

Movement of retaining plate 330, and hence, the PCB being held by retaining plate 330, is accomplished in the embodiment of FIG. 3 by four electric motors 340, the motion of which is controlled by a computer, microcontroller, or some other type of algorithmic controller. Electric motors 340 apply force upward at four diverse positions of retaining plate 330. The top end of electric motors 340 (obscured from view by retaining plate 330) is not rigidly attached to retaining plate 330 so that retaining plate 330 may rotate about any two orthogonal horizontal axes. A round surface at the top end of electric motor 340 may be used for contact with retaining plate 330, as well as any other surface shape or construction that minimizes the possible wear on both electric motors 340 and retaining plate 330.

In many embodiments, the combination of the weight of retaining plate 330 and the action of struts 310 will allow enough force from retaining plate 330 downward onto electric motors 340 so that retaining plate 330 will follow electric motors 340 in the downward direction. Additionally, the downward force applied by retaining plate 330 will be moderate enough so that electric motors 340 may move retaining plate 330 in the upward direction without undue stress on motor 340.

Electric motors 340 may be any electric motors that can be accurately controlled by computer, dedicated electronics, or any other kind of algorithmic control system. For example, standard stepper motors may be utilized to provide accurate positioning of retaining plate 330. Also, servo motors, which are generally faster but possibly less accurate than stepper motors, may be employed. Additionally, to improve the accuracy of any electric motors 340 used, a system of position feedback, such as linear or rotary encoders that are well known in the art, may be utilized in conjunction with electric motors 340. The use of such a position feedback system may be desired depending on the nature of the motors used and the level of positioning accuracy required by the adjustment mechanism.

Although most of the embodiments of the invention herein disclosed display the use of four electric motors 340, fewer such motors may be employed, depending on the particular adjustment mechanism. For example, concerning the embodiment of FIG. 3, three electric motors 340 may be utilized instead of four, so long as the motors are positioned at diverse locations about retaining plate 330 so that all of the translational and rotational motions allowed by the mechanism may be implemented. The use of three electric motors may accomplish this result due to the fact that any three distinct points define a plane in space, which, in this case, is the plane defined by retaining plate 330.

The motion of electric motors 340 is dependent upon which area of the PCB under inspection is being examined. To determine the relative vertical translation and rotational orientation of the PCB desired for a particular area, a system that maps out the surface of the PCB prior to its detailed inspection using the embodiments disclosed herein may be employed to advantage. Such a system is not the focus of the embodiments of the present invention, but the optimal use of the embodiments may benefit from the utilization of such a system.

Figure 5:
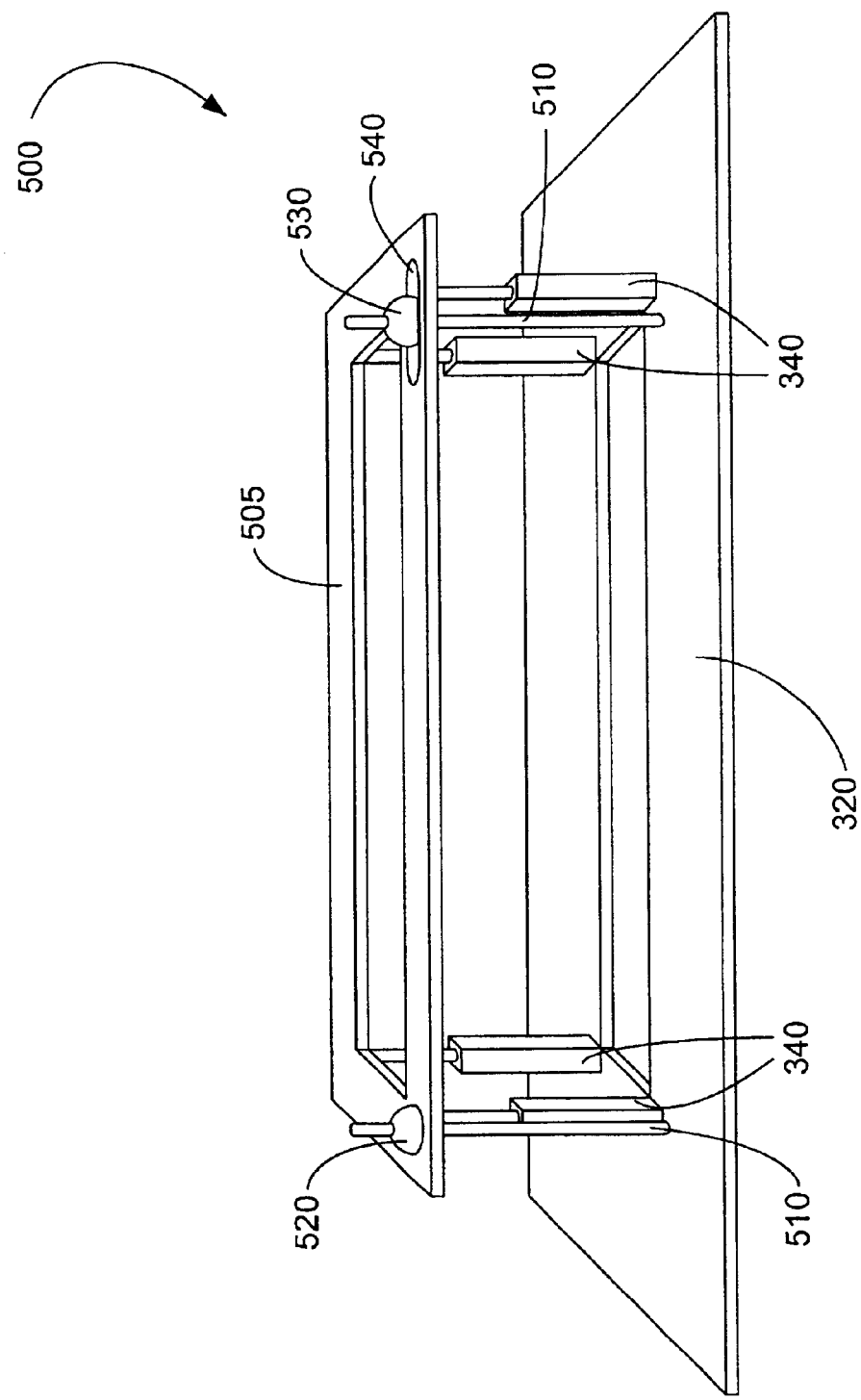
FIG. 5 is a perspective view of an adjustment mechanism according to an embodiment of the invention that utilizes a stationary ball joint and a sliding ball joint to allow a PCB under inspection to translate vertically and rotate about two horizontal axes while restricting both horizontal translation and rotation about a vertical axis.

Another embodiment of the invention is adjustment mechanism 500, which is displayed in FIG. 5. Instead of struts, adjustment mechanism 500 utilizes two vertical shafts 510 mounted at their bottom ends to a stable base 320, as first mentioned in conjunction with the embodiment of FIG. 3. Near the top end of vertical shafts 510 reside a first sliding ball 520 and a second sliding ball 530, each of which may slide vertically along its respective vertical shaft 510. First sliding ball 520 is mounted within retaining plate 505, which is similar to retaining plate 330 shown in FIG. 3, in such a way that first sliding ball 520 is allowed to rotate within retaining plate 505, resulting in a fixed-position ball joint that allows rotational movement, but prohibits any substantial horizontal translation of retaining plate 505.

Second sliding ball 530, unlike first ball 520, may move translationally along a linear slot 540 which resides along the line defined by vertical shafts 510, allowing rotation about a horizontal axis orthogonal to the line defined by first and second sliding balls 520 and 530. Second sliding ball 530 also allows vertical translation along its vertical shaft 510, as well as rotation about the line defined by first and second sliding balls 520 and 530. As a result of such a motion guiding structure, rotation about the vertical axis and any horizontal translation are substantially limited, in similar fashion to that exhibited by the embodiment of FIG. 3.

Electric motors 340, from FIG. 3, are also used in adjustment mechanism 500. Additionally, as few as three electric motors 340 may be used, in a fashion similar to that described for adjustment mechanism 300 from FIG. 3.

Figure 6:
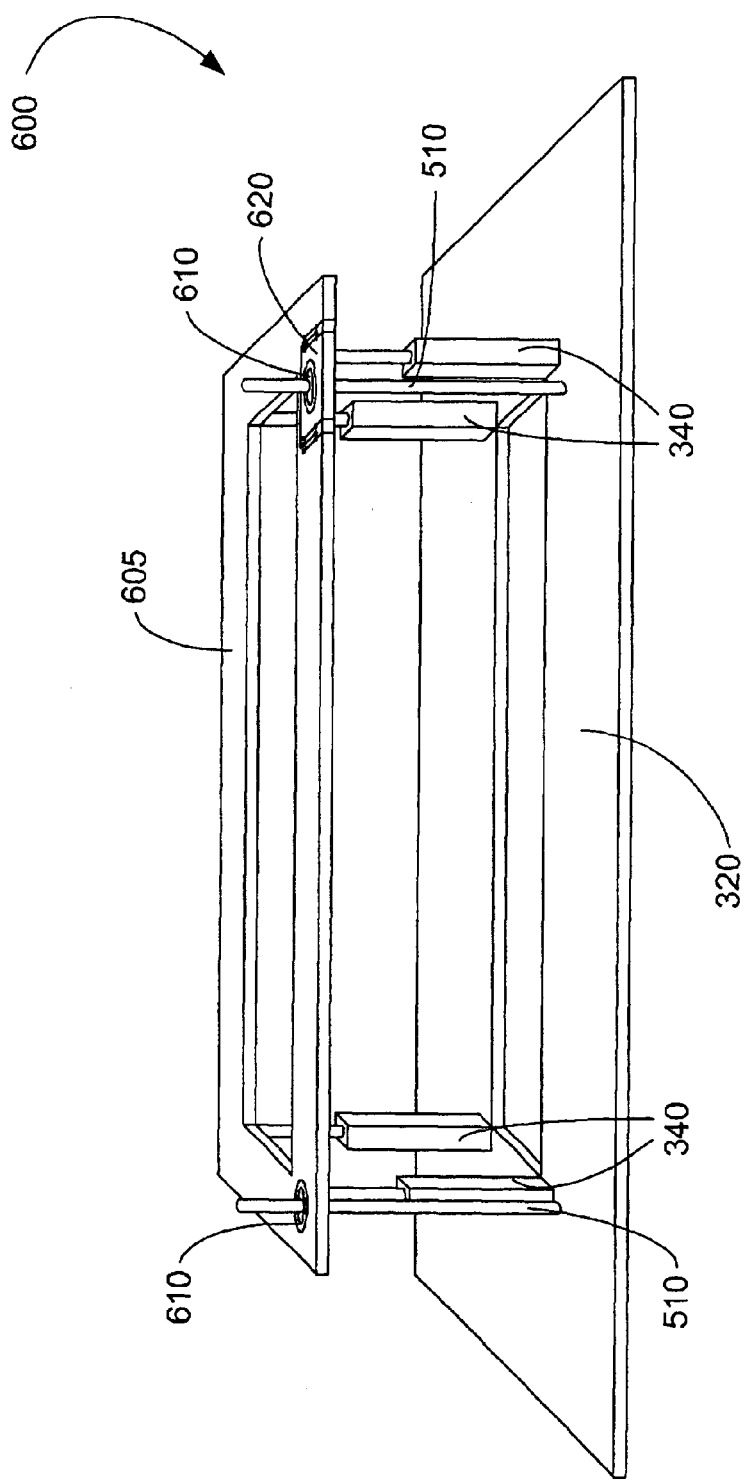
FIG. 6 is a perspective view of an adjustment mechanism according to an embodiment of the invention that utilizes two fixed bearing joints, one of which is mounted within a flexure mounting, that allow a PCB under inspection to translate vertically and rotate about two horizontal axes while restricting both horizontal translation and rotation about a vertical axis.

Another embodiment, adjustment mechanism 600, displayed in FIG. 6, employs a similar concept using two vertical shafts 510 attached at their bottom ends to stable base 320. However, instead of balls slidably mounted on vertical shafts 510, a pair of pivot bearings 610 is employed. First pivot bearing 610 is mounted in a stationary manner in a retaining plate 605, which is similar to the retaining plates of the embodiments shown above. Second pivot bearing 610 is mounted within a flexure mounting 620 or similar structure incorporated within retaining plate 605. One possible example of pivot bearing 610 is a spherical plain radial bearing, type SF, manufactured by The Torrington Company. Other similar structures that could possibly be used in this capacity include a sliding stage incorporated within retaining plate 605 that allows the same left and right movement as flexure mounting 620. Such a sliding stage would utilize ball bearings or dovetail joints to allow low-friction movement of the stage within retaining plate 605.

Figure 7:
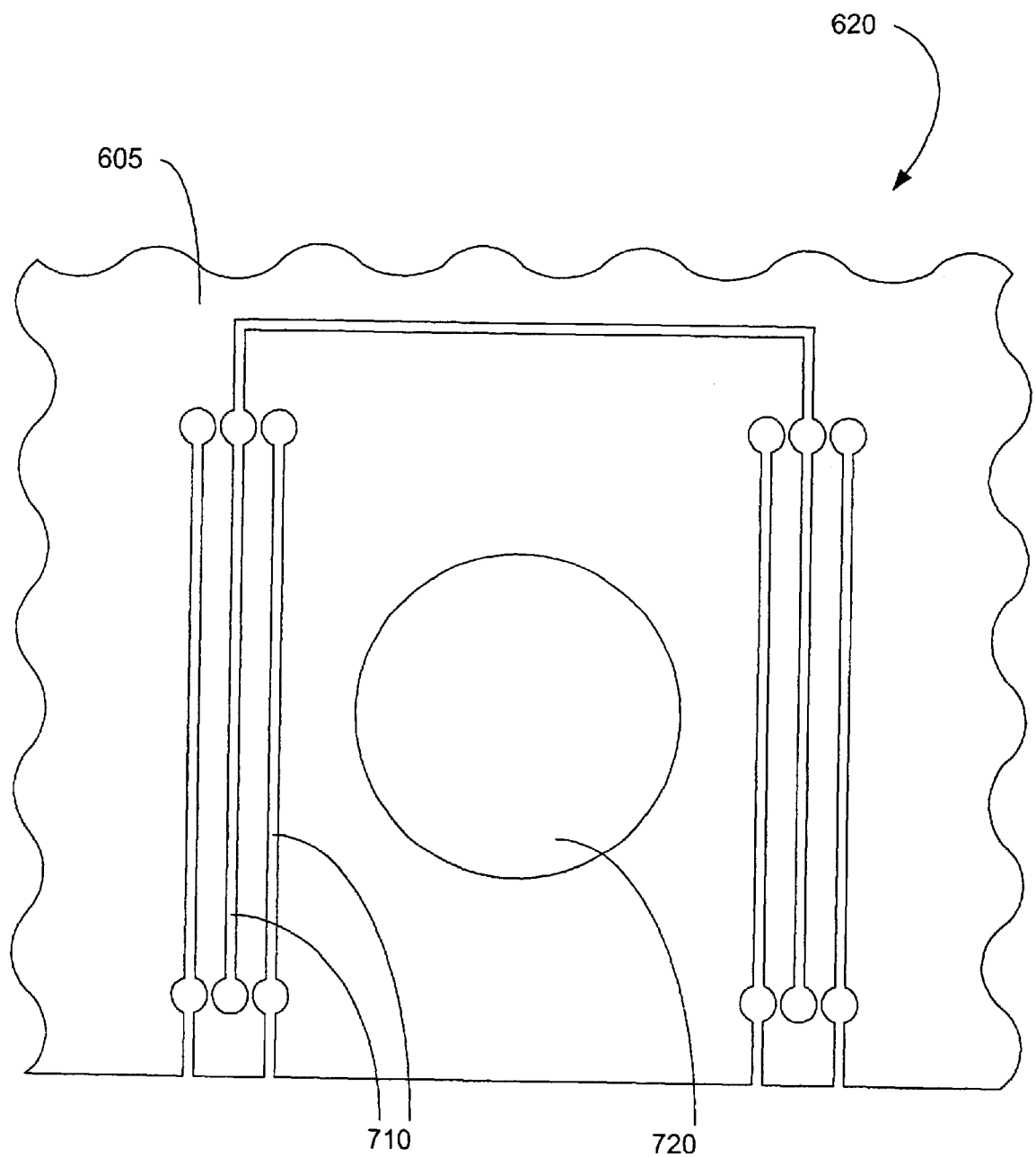
FIG. 7 is a top view of the flexure mounting shown in FIG. 6.

A more detailed view of flexure mounting 620 from FIG. 6 is depicted in FIG. 7. In this particular embodiment, gaps 710 are cut or manufactured into retaining plate 605 so that second pivot bearing 610, residing within a hole 720, may move slightly left or right to compensate for any rotation of retaining plate 605 about a horizontal axis transverse to the line defined by first and second pivot bearings 610. Such a flexure mounting is new for this particular application, although similar flexure mountings have been used in other applications in the prior art.

As a result of vertical shafts 510, pivot bearings 610, and flexure mounting 620, retaining plate 605 may translate vertically, as well as rotate horizontally about two orthogonal horizontal axes. Also, similar to the previous embodiments discussed above, horizontal translation, as well as rotation about the vertical axis, is substantially limited.

Four electric motors 340 are used to move retaining plate 605 into proper position for inspection of an area of the PCB being analyzed. As few as three motors may be used, as discussed for the previous embodiments.

Figure 8:
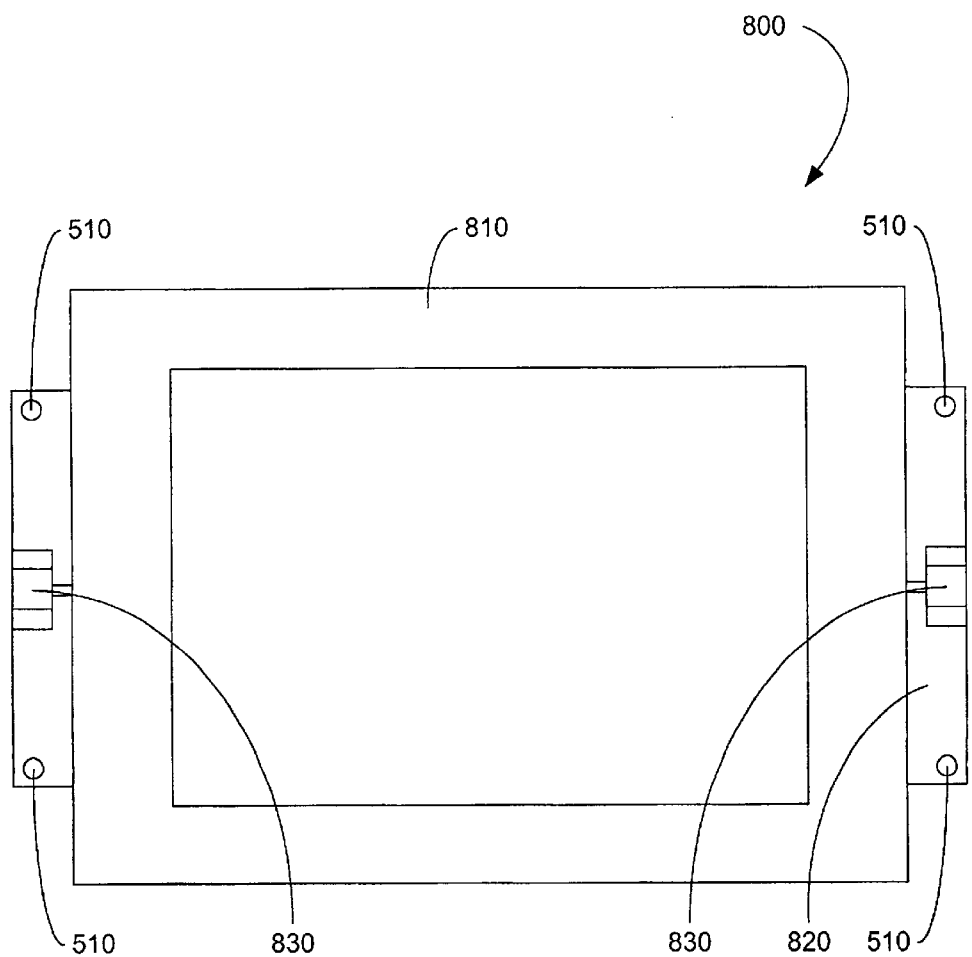
FIG. 8 is a top view of an adjustment mechanism according to an embodiment of the invention that utilizes two sets of pivot joints that allows a PCB under inspection to rotate about each of two orthogonal horizontal axes while restricting both horizontal translation and rotation about a vertical axis.
Figure 9:
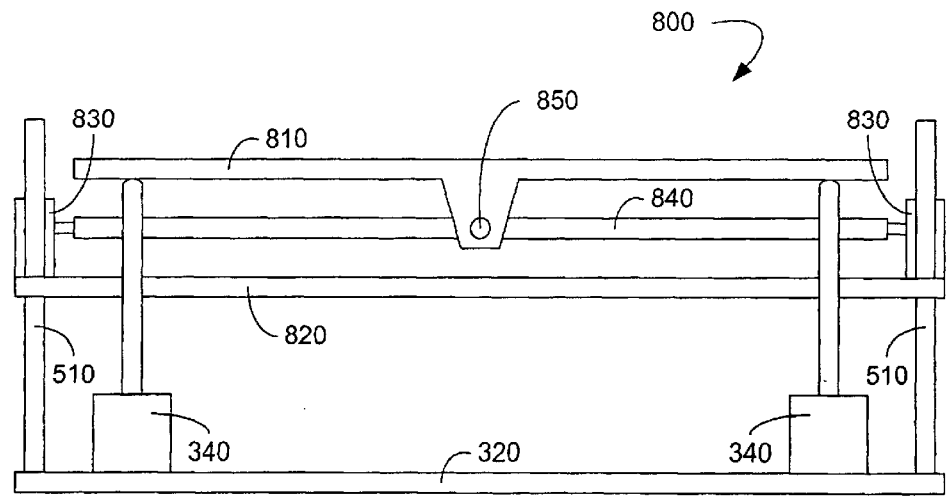
FIG. 9 is a front view of the adjustment mechanism of FIG. 8.
Figure 10:
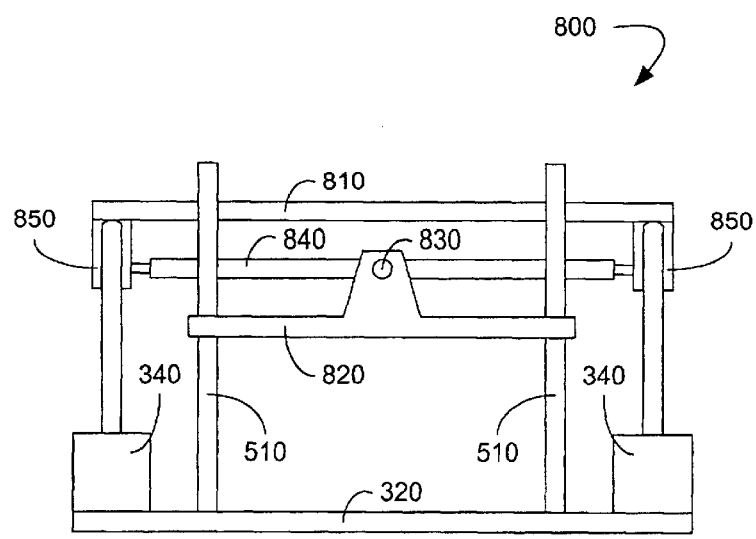
FIG. 10 is a side view of the adjustment mechanism of FIG. 8.

Another embodiment of the invention, in the form of adjustment mechanism 800, is shown in FIG. 8 (top view), FIG. 9 (front view), and FIG. 10 (side view). As stated for earlier embodiments, four vertical shafts 510 are attached at their bottom ends to a stable base 320. For adjustment mechanism 800, a first coupling plate 820 defines four holes (not explicitly shown) through which vertical shafts 510 protrude so that first coupling plate 820 is held substantially in a horizontal orientation while allowing vertical translation of first coupling plate 820 along shafts 510.

A second coupling plate 840 is coupled with first coupling plate 820 by way of a set of first pivot joints 830, allowing second coupling plate 840 to rotate about the horizontal axis defined by first pivot joints 830. Depending on the specific demands of the object being inspected, only one first pivot joint 830 may be employed.

A retaining plate 810, in a fashion similar to the retaining plates described earlier, holds a PCB to be inspected. Retaining plate 810 is coupled to second coupling plate 840 by way of a pair of second pivot joints 850, which define a rotational axis perpendicular to that defined by first pivot joints 830. That configuration thus allows retaining plate 810 to rotate about two orthogonal horizontal axes defined by the plane of first coupling plate 820. As a result, retaining plate 810 is allowed a similar range of motion as in the previous embodiments, while restricting any substantial horizontal translation or rotation about the vertical axis as a result of vertical shafts 510.

Also, in similar fashion to the previous embodiments mentioned, at least three electric motors 340 translate retaining plate 810 into proper position for inspection of an area of the PCB to be viewed. Four such motors 340 are employed in the embodiment described by adjustment mechanism 800. Additionally, as in the previous examples, motors 340 are not rigidly attached to retaining plate 810, as any rotation of retaining plate 810 causes the point at which motors 340 contact retaining plate 810 to migrate slightly.

Figure 11:
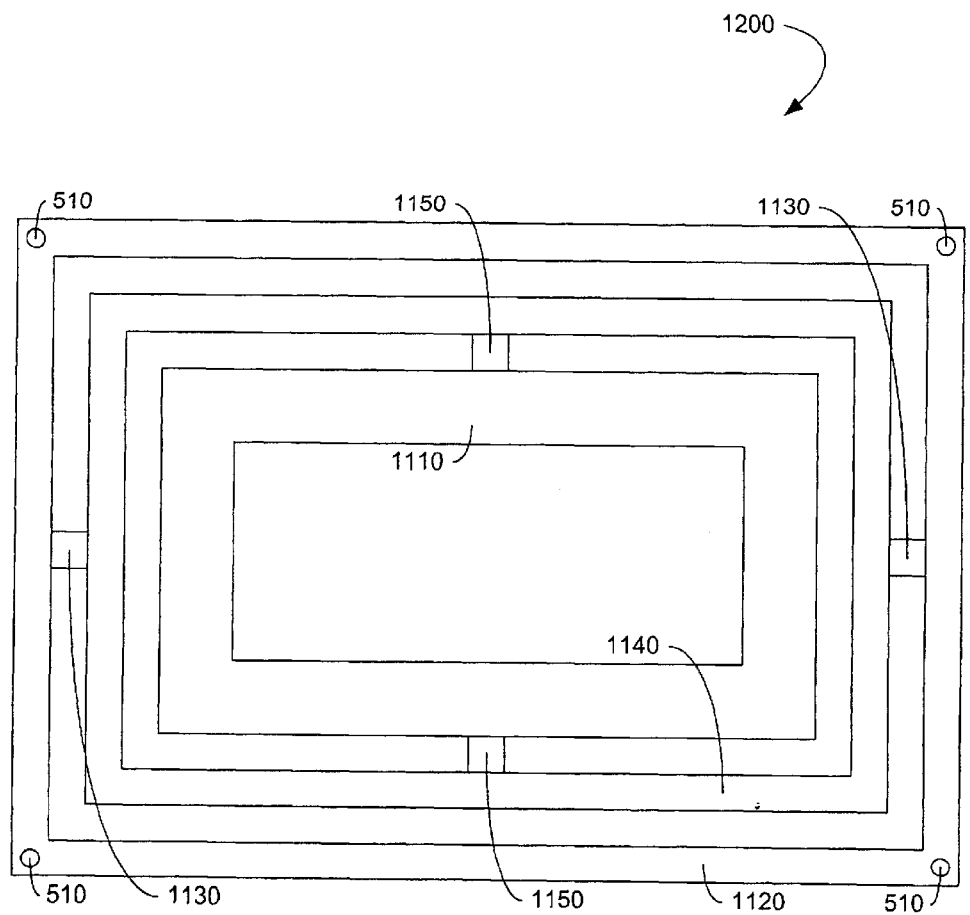
FIG. 11 is a top view of an adjustment mechanism according to another embodiment of the invention that is based on the embodiment of FIG. 8, FIG. 9, and FIG. 10.

FIG. 11 provides a top view of adjustment mechanism 1100, which is a variation of the embodiment of FIGS. 8, 9, and 10, wherein a retaining plate 1110, a first coupling plate 1120, and a second couple plate 1140 all lie substantially in the same plane, by way of centrally-located holes in first and second coupling plates 1120 and 1140, to keep the height required by adjustment mechanism 1100 to a minimum. First coupling plate 1120 contains holes through which vertical shafts 510 protrude. Vertical shafts 510 are connected at their bottom ends to a stable base (not shown), thus allowing first coupling plate 1120 to translate vertically without any other substantial translation or rotation involved. Second coupling plate 1140, located within first coupling plate 1120, is coupled with first coupling plate 1120 via a pair of first pivot joints 1130. Depending on the particular application, only one of first pivot joints 1130 may be necessary. First pivot joints 1130 allow second coupling plate 1140 to rotate about a horizontal axis defined by first pivot joints 1130. In turn, second pivot joints 1150 couple retaining plate 1110 with second coupling plate 1140, allowing retaining plate 1110 to rotate about a second horizontal axis perpendicular to the first horizontal axis. A minimum of three electric motors (not shown) that are analogous to those use in the previous embodiments apply force in the vertical direction on retaining plate 1110 to enable vertical translation and rotation about either of the orthogonal horizontal axes, while substantially restricting other translation and rotation, in a fashion similar to the embodiment of FIGS. 8, 9, and 10.

Figure 12:
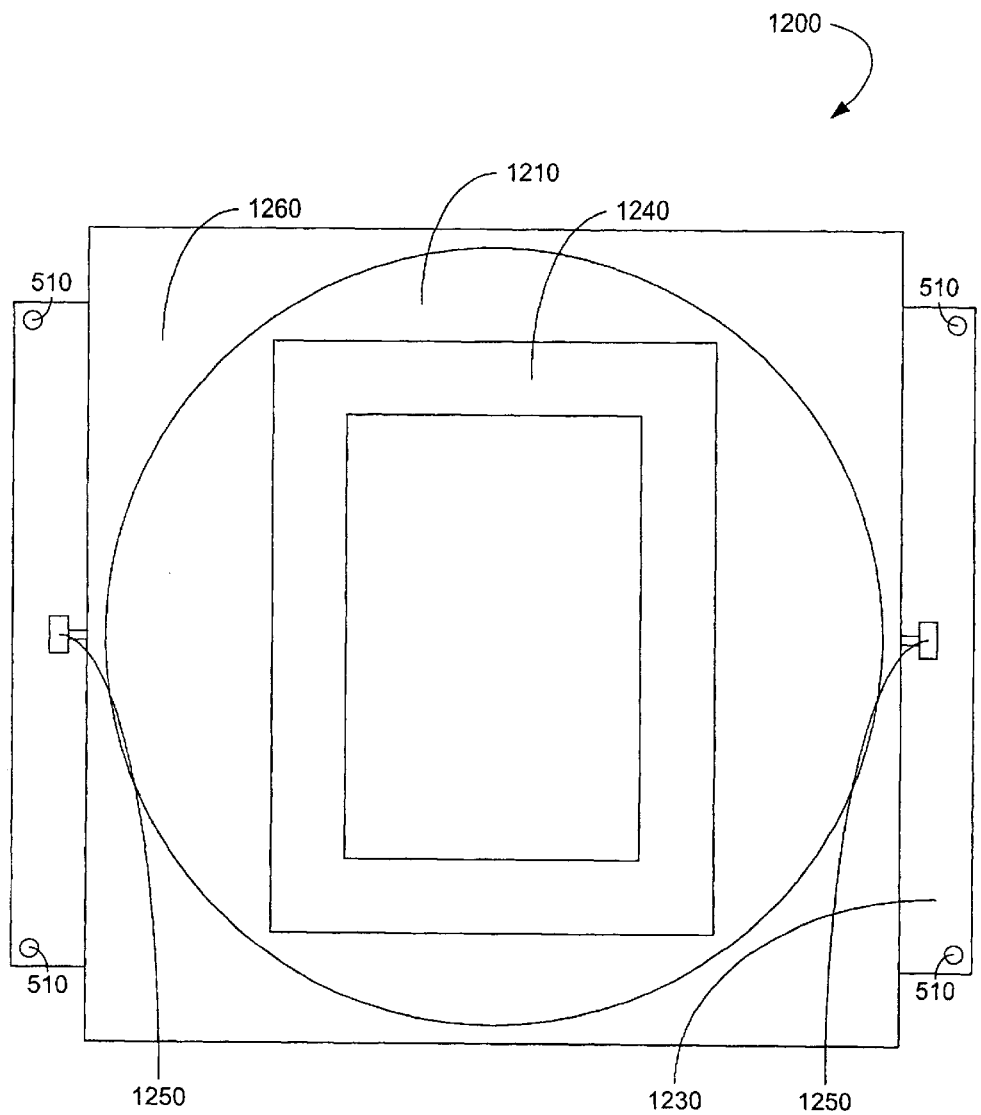
FIG. 12 is a top view of an adjustment mechanism according to an embodiment of the invention that utilizes a set of pivot joints in combination with a turntable so that the pivot joints will allow rotation about a horizontal axis of the turntable, which, in turn, causes a PCB under inspection to rotate about a vertical axis.
Figure 13:
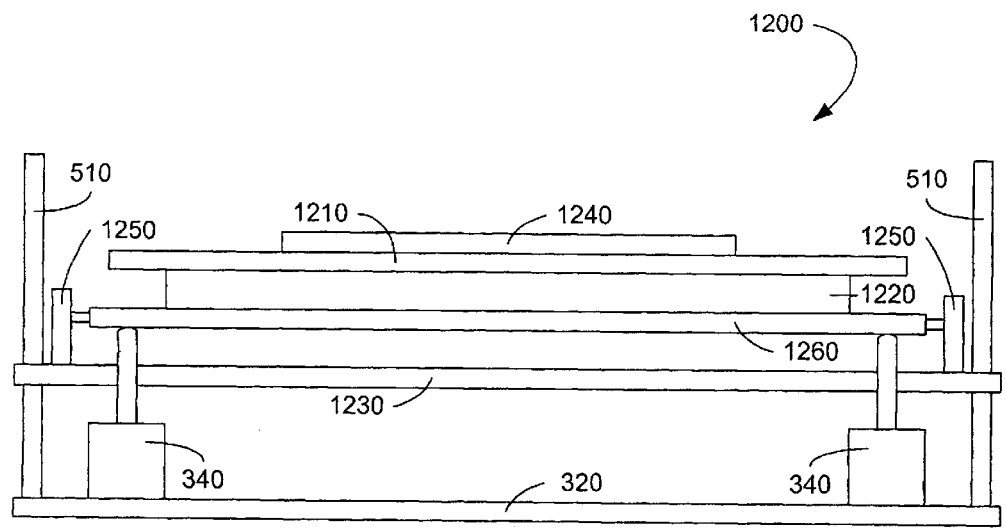
FIG. 13 is a front view of the adjustment mechanism of FIG. 11.
Figure 14:
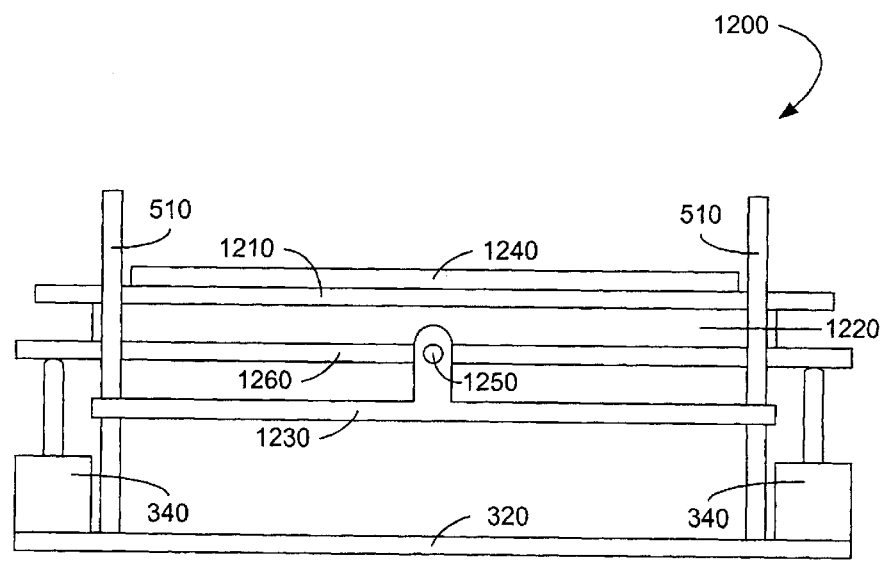
FIG. 14 is a side view of the adjustment mechanism of FIG. 11.

Another embodiment, in the form of adjustment mechanism 1200, takes a slightly different approach from that shown in previous embodiments. As depicted in FIG. 12 (top view), FIG. 13 (front view), and FIG. 14 (side view), adjustment mechanism 1200 is comprised of, in part, a turntable 1210 selectively driven by a rotational electric motor 1220.

Four vertical shafts 510 are connected at their bottom ends to a stable base 320. Vertical shafts 510 also protrude through holes defined by coupling plate 1230, thus allowing coupling plate 1230 to translate vertically along shafts 510, with all other translational and rotational movement of coupling plate 1230 substantially limited with respect to stable base 320.

A turntable base 1260 is coupled with coupling plate 1230 by use of a pair of pivot joints 1250. Again, depending on the particular application for adjustment mechanism 1200, only one pivot joint 1250 may be sufficient. Pivot joints 1250 allow turntable base 1260 to pivot about the horizontal axis defined by pivot joints 1250. Such pivoting, as well as vertical translation, is accomplished via the action of electric motors 340, which have essentially the same characteristics as those presented in the embodiments described above. Four electric motors 340 are utilized in adjustment mechanism 1210, although as few as two are contemplated, as only vertical translation and pivoting about a single horizontal axis are required of electric motors 340.

Attached to turntable base 1260 via rotational electric motor 1220 is a turntable 1210, to which a retaining plate 1240 is attached. In an alternative embodiment, retaining plate 1240 may be attached directly to rotational electric motor 1220. In order to allow retaining plate 1240 to be able to rotate about any two orthogonal horizontal axes to facilitate optimum focus for irregular PCB surfaces, rotational electric motor 1220 turns turntable 1210 and retaining plate 1240 so that pivoting of turntable base 1260 about pivot joints 1250 will allow the area of interest of the PCB under inspection to lie within the depth of focus. Unlike the previous embodiments, the horizontal translational position of the area of interest may vary substantially from neighboring areas of interest, depending on the shape of the PCB surface, requiring the inspection system to closely monitor the rotation of retaining plate 1240 about the vertical axis.

The freedom of movement required by rotational electric motor 1220 depends in part on the rotational ability of pivot joints 1250. For example, if pivot joints 1250 allow the tilting of turntable base 1260 on either side of the horizontal position, rotational electric motor 1220 is only required to rotate turntable base 1260 through a maximum of ninety degrees in order for adjustment mechanism 1200 to handle a warping of the PCB under inspection in any direction along its surface. Conversely, if pivot joints 1250 allow tilting only to one side of the horizontal position, rotational electric motor 1220 is required to provide 180 degrees of rotation to compensate for the more restrictive movement of pivot joints 1250.

Additionally, rotational electric motor 1220 is toroidal in nature. In other words, rotational electric motor 1220 defines a centrally-located hole (not shown in the figures) which allows unimpeded line-of-sight over the entire area of the PCB between an x-ray source and detector through adjustment mechanism 1200.

Figure 15:
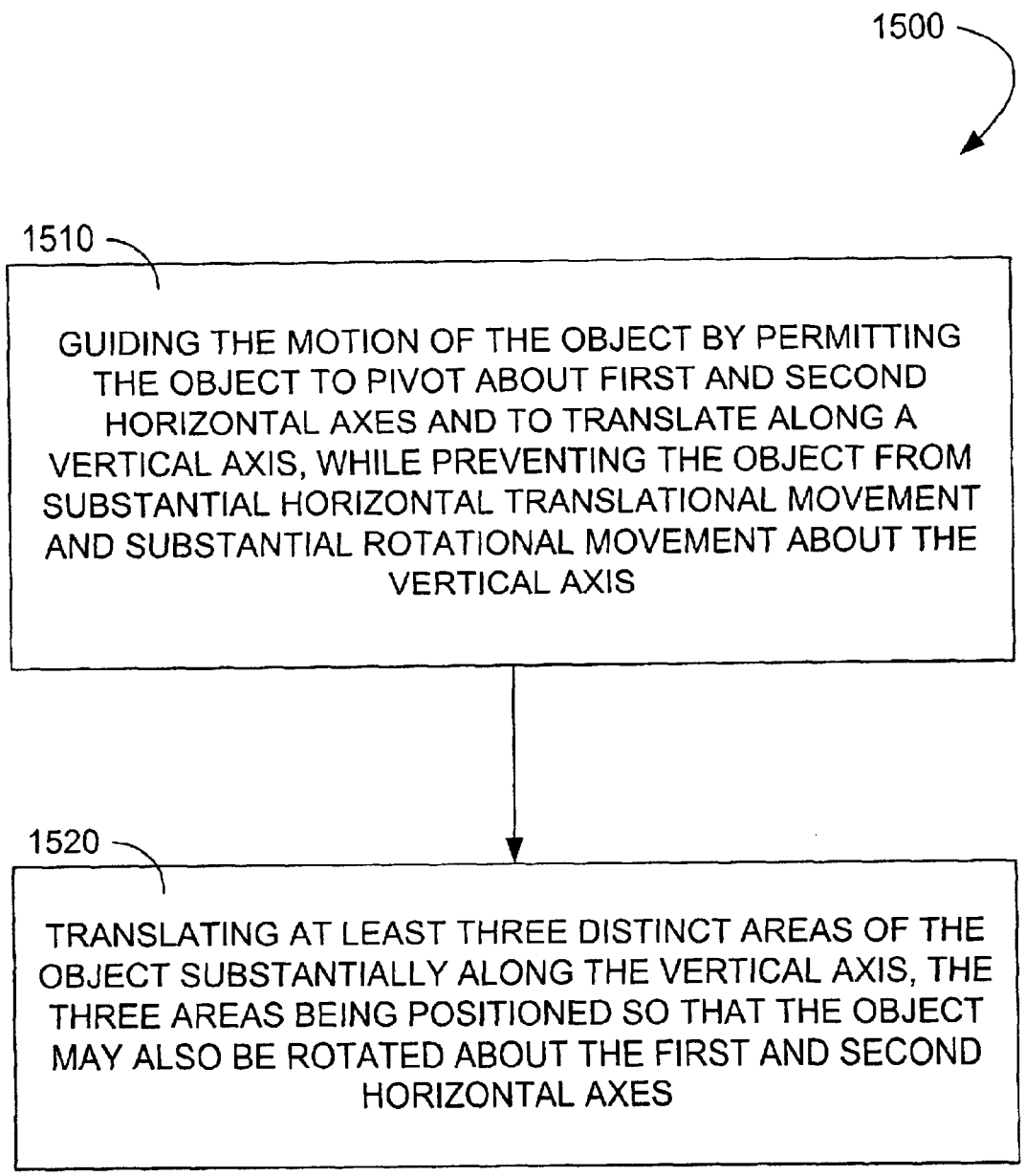
FIG. 15 is a flowchart of a method of position and rotation adjustment according to an embodiment of the invention.

Some embodiments of the invention take the form of methods of adjusting the translational position and rotational orientation of an object. For example, as shown in FIG. 15, method 1500 is utilized to adjust the location of an object, such as a PCB under inspection, along a vertical axis and the rotational orientation of the object about a first and second horizontal axes that are orthogonal to the vertical axis and to each other. Potential motion of the object is guided so that the object may pivot about either of the horizontal axes and translate along the vertical axis, while any other substantial translational or rotational movement is prevented (step 1510). At least three distinct areas of the object are translated along the vertical axis, with those three areas being positioned so that the object may also be rotated about the horizontal axes (step 1520). Such translation allows the object to be place in a predetermined vertical location and rotational orientation about the horizontal axes to suit the particular application in which the method in employed.

Figure 16:
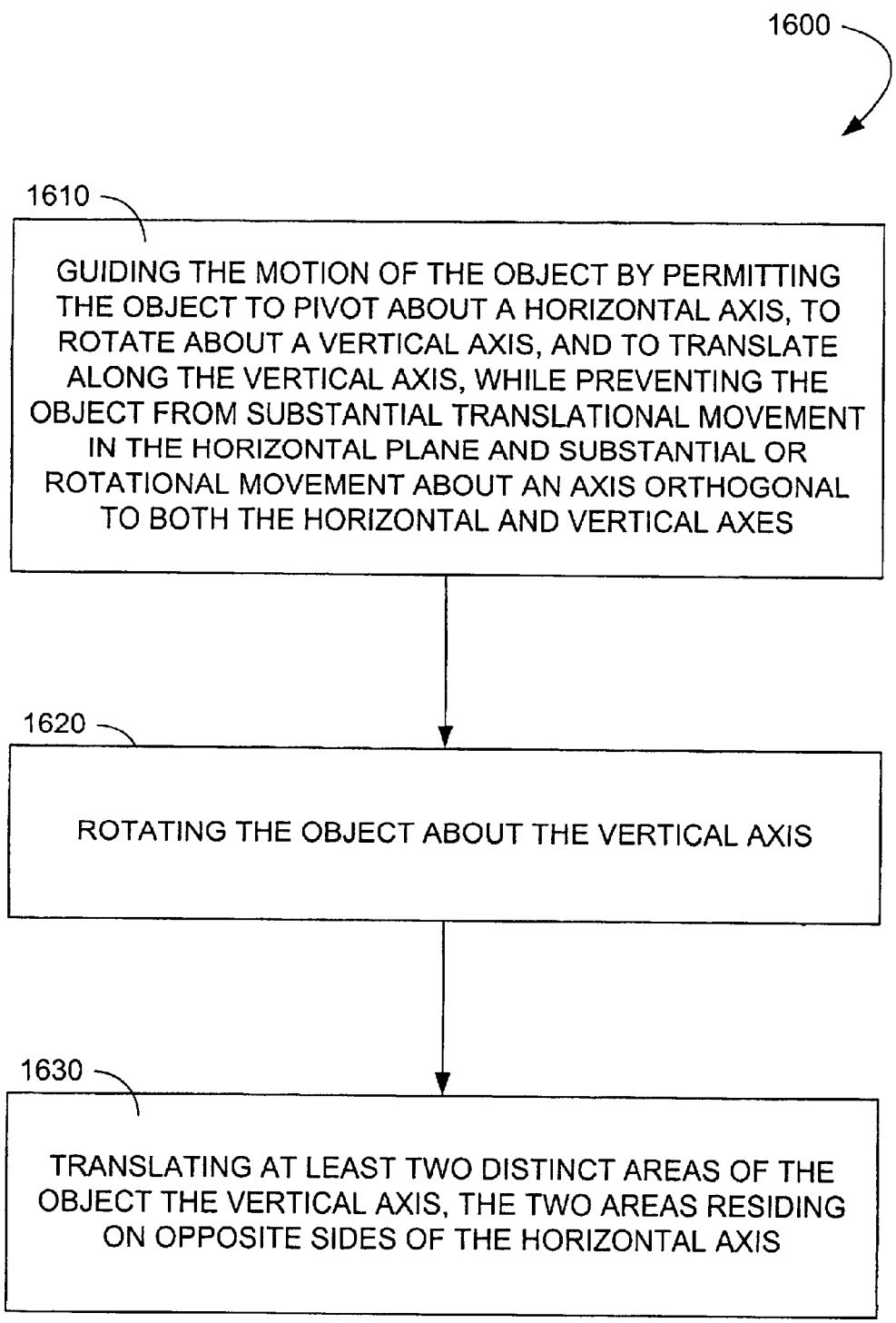
FIG. 16 is a flowchart of another method of position and rotation adjustment according to an embodiment of the invention.

Another method embodiment, as depicted in the flowchart of FIG. 16, may be employed to adjust the location of an object along a vertical axis, as well as the rotational orientation of the object about the vertical axis and a horizontal axis that is orthogonal to the vertical axis. Potential motion of the object is guided so that the object may pivot about the horizontal axis, rotate about the vertical axis, and translate along the vertical axis, while preventing any other substantial translational or rotational movement (step 1610). The object is also rotated about the vertical axis (step 1620). Also, two distinct areas of the object are translated along the vertical axis, with the two areas residing on opposite sides of the horizontal axis (step 1630). As a result, the interaction of the rotating and translating steps cause the object to be placed in a predetermined vertical location and rotational orientation about the vertical and horizontal axes.

From the foregoing, the embodiments of the invention discussed above have been shown to provide an adjustment mechanism which not only allows translational movement to position an item under inspection at the proper focal distance from an image-based inspection source, but also effectively allows rotational movement so that more area of an irregular surface of the item may lie within the depth of focus associated with the inspection system. In addition, other specific systems and methods embodying the invention are also possible. Therefore, the present invention is not to be limited to the specific forms so described and illustrated; the invention is limited only by the claims.

What is claimed is:

1. A mechanism for adjusting both the location of an object along a vertical axis and the rotational orientation of the object about a first and second horizontal axes, the first and second horizontal axes each being orthogonal to the vertical axis and to each other, the mechanism comprising:

means for retaining the object;

means for guiding motion of the retaining means, the guiding means permitting the retaining means to pivot about the first and second horizontal axes, the guiding means also permitting the retaining means to translate along the vertical axis, the guiding means preventing the retaining means from substantial translational movement in the plane defined by the first and second horizontal axes and substantial rotational movement about the vertical axis; and means for translating at least three distinct areas of the retaining means substantially along the vertical axis, the three areas being positioned so that the retaining means may also be rotated about the first and second horizontal axes by the translating means, the object thus residing in a predetermined vertical location and rotational orientation about the horizontal axes.

2. The adjusting mechanism of claim 1, wherein the retaining means is a retaining plate designed to securely hold a printed circuit board.

3. The adjusting mechanism of claim 1, wherein the guiding means comprises at least three struts coupled at separate points around the perimeter of the retaining means, the struts extending outward and downward from the retaining means, the struts coupling the retaining means with a stable base.

4. The adjusting mechanism of claim 3, wherein the stable base is a horizontal translation table capable of translating the adjusting mechanism horizontally.

5. The adjusting mechanism of claim 1, wherein the guiding means comprises:

a first ball slidably mounted on a first vertical shaft mounted at the bottom end to a stable base, the first ball coupled with the retaining means to form a fixed-position ball joint wherein the first ball may rotate within a single position within the retaining means; and a second ball slidably mounted on a second vertical shaft mounted at the bottom end to the stable base, the second ball coupled with the retaining means to form a sliding ball joint wherein the second ball may rotate and slide within a linear slot within the retaining means, the first ball lying within the line defined by the linear slot.

6. The adjusting mechanism of claim 5, wherein the stable base is a horizontal translation table capable of translating the adjusting mechanism horizontally.

7. The adjusting mechanism of claim 1, wherein the guiding means comprises:

a first pivot bearing slidably mounted on a first vertical shaft mounted at the bottom end to a stable base, the first pivot bearing coupled with the retaining means in a stationary manner that permits the retaining means to pivot about the two orthogonal horizontal axes; and a second pivot bearing slidably mounted on a second vertical shaft mounted at the bottom end to the stable base, the second pivot bearing coupled with the retaining means by way of a flexure mounting to permit the retaining means to rotate about a horizontal axis perpendicular to the axis defined by the first and second pivot bearings.

8. The adjusting mechanism of claim 7, wherein the stable base is a horizontal translation table capable of translating the adjusting mechanism horizontally.

9. The adjusting mechanism of claim 1, wherein the guiding means comprises:

at least two vertical shafts rigidly attached at the bottom end to a stable base;

a first coupling plate defining a hole for each vertical shaft, the shafts protruding through the holes so that the first coupling plate is held in a substantially horizontal fashion while being allowed to translate vertically;

a second coupling plate;

a first pivot joint coupling the first coupling plate with the second coupling plate, the first pivot joint permitting the second coupling plate to rotate only about the first horizontal axis; and a second pivot joint coupling the second coupling plate with the retaining means, the second pivot joint permitting the retaining means to rotate only about an axis orthogonal to the first horizontal axis and parallel to the second coupling plate.

10. The adjusting mechanism of claim 9, wherein the stable base is a horizontal translation table capable of translating the adjusting mechanism horizontally.

11. The adjusting mechanism of claim 9, wherein the first and second coupling plates define centrally-located holes large enough so that the retaining means and the first and second coupling plates all lie within a single plane when the retaining means is oriented horizontally.

12. The adjusting mechanism of claim 1, wherein the translating means comprises at least three electric motors attached to a stable base, with each of the electric motors applying force to the retaining means along the vertical axis to the at least three distinct areas of the retaining means.

13. The adjusting mechanism of claim 12, wherein the electric motors are servo motors.

14. The adjusting mechanism of claim 12, wherein the electric motors are stepper motors.

15. The adjusting mechanism of claim 1, further comprising at least one spring compressed between a stable base and the guiding means to reduce the force required by the translating means to translate the retaining means upward along the vertical axis.

16. The adjusting mechanism of claim 1, further comprising at least one counterweight assembly applying force upward against the guiding means to reduce the force required by the translating means to translate the retaining means upward along the vertical axis.

17. A mechanism for adjusting both the location of an object along a vertical axis and the rotational orientation of the object about the vertical axis and a horizontal axis that is orthogonal to the vertical axis, the mechanism comprising:

means for retaining the object;

means for rotating the retaining means about the vertical axis;

means for guiding the movement of the rotating means, the guiding means permitting the rotating means to pivot about the horizontal axis, the guiding means also permitting the rotating means to translate along the vertical axis, the guiding means preventing the rotating means from substantial translational movement in the horizontal plane and substantial rotational movement about either the vertical axis or an axis orthogonal to both the horizontal and vertical axes; and means for translating at least two distinct areas of the rotating means along the vertical axis, the two areas residing on opposite sides of the horizontal axis, the translating means being capable of translating the rotating means along the vertical axis and pivoting the rotating means about the horizontal axis, the object thus residing in a predetermined vertical location and rotational orientation about the horizontal and vertical axes.

18. The adjusting mechanism of claim 17, wherein the retaining means is a retaining plate designed to securely hold a printed circuit board.

19. The adjusting mechanism of claim 17, wherein the guiding means comprises:

at least two vertical shafts rigidly attached at the bottom end to a stable base;

a coupling plate defining a hole for each vertical shaft, the shafts protruding through the holes so that the coupling plate is held in a substantially horizontal fashion while being allowed to translate vertically;

a pivot joint coupling the coupling plate with the rotating means, the pivot joint permitting the rotating means to pivot about the horizontal axis.

20. The adjusting mechanism of claim 19, wherein the stable base is a horizontal translation table capable of translating the adjusting mechanism horizontally.

21. The adjusting mechanism of claim 17, wherein the rotating means is a turntable driven by a rotational electric motor, the rotational electric motor being supported by a turntable base.

22. The adjusting mechanism of claim 17, wherein the translating means comprises at least two electric motors attached to the stable base, with each of the electric motors applying force to the rotating means along the vertical axis in at the least two distinct areas of the rotating means.

23. The adjusting mechanism of claim 22, wherein the electric motors are servo motors.

24. The adjusting mechanism of claim 22, wherein the electric motors are stepper motors.

25. The adjusting mechanism of claim 17, further comprising at least one spring compressed between a stable base and the guiding means to reduce the force required by the translating means to translate the rotating means upward along the vertical axis.

26. The adjusting mechanism of claim 17, further comprising at least one counterweight assembly applying force upward against the guiding means to reduce the force required by the translating means to translate the rotating means upward along the vertical axis.

27. A mechanism for adjusting both the location of a printed circuit board along a vertical axis and the rotational orientation of the printed circuit board about a first and second horizontal axes, the first and second horizontal axes each being orthogonal to the vertical axis and to each other, the mechanism comprising:

a retaining plate designed to securely hold the printed circuit board;

a mechanical guiding structure, the guiding structure permitting the retaining plate to pivot about the first and second horizontal axes, the guiding structure also permitting the retaining plate to translate along the vertical axis, the guiding structure preventing the retaining plate from substantial translational movement in the plane defined by the first and second horizontal axes and substantial rotational movement about the vertical axis; and at least three electric motors, with each applying force to the retaining plate along the vertical axis to at least three distinct areas, the three areas being positioned so that the retaining plate may be rotated about the first and second horizontal axes by the electric motors, the printed circuit board thus residing in a predetermined vertical location and rotational orientation about the horizontal axes.

28. The adjusting mechanism of claim 27, wherein the mechanical guiding structure comprises at least three struts coupled at separate points around the perimeter of the retaining plate, the struts extending outward and downward from the retaining plates, the struts coupling the retaining plate with a stable base.

29. The adjusting mechanism of claim 28, wherein the stable base is a horizontal translation table capable of translating the adjusting mechanism horizontally.

30. The adjusting mechanism of claim 27, wherein the mechanical guiding structure comprises:

a first ball slidably mounted on a first vertical shaft mounted at the bottom end to a stable base, the first ball coupled with the retaining plate to form a fixed-position ball joint wherein the first ball may rotate within a single position within the retaining plate; and a second ball slidably mounted on a second vertical shaft mounted at the bottom end to the stable base, the second ball coupled with the retaining plate to form a sliding ball joint wherein the second ball may rotate and slide within a linear slot within the retaining plate, the first ball lying within the line defined by the linear slot.

31. The adjusting mechanism of claim 30, wherein the stable base is a horizontal translation table capable of translating the adjusting mechanism horizontally.

32. The adjusting mechanism of claim 27, wherein the mechanical guiding structure comprises:

a first pivot bearing slidably mounted on a first vertical shaft mounted at the bottom end to a stable base, the first pivot bearing coupled with the retaining plate in a stationary manner that permits the retaining plate to pivot about the two orthogonal horizontal axes; and a second pivot bearing slidably mounted on a second vertical shaft mounted at the bottom end to the stable base, the second pivot bearing coupled with the retaining plate by way of a flexure mounting to permit the retaining plate to rotate about a horizontal axis perpendicular to the axis defined by the first and second pivot bearings.

33. The adjusting mechanism of claim 32, wherein the stable base is a horizontal translation table capable of translating the adjusting mechanism horizontally.

34. The adjusting mechanism of claim 27, wherein the mechanical guiding structure comprises:

at least two vertical shafts rigidly attached at the bottom end to a stable base;

a first coupling plate defining a hole for each vertical shaft, the shafts protruding through the holes so that the first coupling plate is held in a substantially horizontal fashion while being allowed to translate vertically;

a second coupling plate;

a first pivot joint coupling the first coupling plate with the second coupling plate, the first pivot joint permitting the second coupling plate to rotate only about the first horizontal axis; and a second pivot joint coupling the second coupling plate with the retaining plate, the second pivot joint permitting the retaining plate to rotate only about an axis orthogonal to the first horizontal axis and parallel to the second coupling plate.

35. The adjusting mechanism of claim 34, wherein the stable base is a horizontal translation table capable of translating the adjusting mechanism horizontally.

36. The adjusting mechanism of claim 34, wherein the first and second coupling plates define centrally-located holes large enough so that the retaining plate and the first and second coupling plates all lie within a single plane when the retaining plate is oriented horizontally.

37. The adjusting mechanism of claim 27, wherein the electric motors are servo motors.

38. The adjusting mechanism of claim 27, wherein the electric motors are stepper motors.

39. The adjusting mechanism of claim 27, further comprising at least one spring compressed between a stable base and the mechanical guiding structure to reduce the force required by the electric motors to translate the retaining plate upward along the vertical axis.

40. The adjusting mechanism of claim 27, further comprising at least one counterweight assembly applying force upward against the mechanical guiding structure to reduce the force required by the electric motors to translate the retaining plate upward along the vertical axis.

41. An x-ray laminography inspection system for inspecting a printed circuit board, comprising:

the adjustment mechanism of claim 27, the adjustment mechanism holding the printed circuit board;

a horizontal translation table attached to the adjustment mechanism;

an algorithmic controller that controls the movement of the adjustment mechanism and the horizontal translation table;

an x-ray source located near one side of the printed circuit board; and an x-ray detector, the printed circuit board located between the x-ray source and the x-ray detector, the adjustment mechanism and the horizontal translation table positioning and orienting the printed circuit board so that an area of the printed circuit board being inspected lies substantially within the depth of focus of a focal plane located between and defined by the location of the x-ray source and the x-ray detector.

42. A mechanism for adjusting both the location of a printed circuit board along a vertical axis and the rotational orientation of the printed circuit board about the vertical axis and a horizontal axis that is orthogonal to the vertical axis, the mechanism comprising:

a retaining plate designed to securely hold the printed circuit board;

a turntable driven by a rotational electric motor, the rotational electric motor being supported by a turntable base;

a mechanical guiding structure that guides the movement of the turntable base, the guiding structure permitting the turntable base to pivot about the horizontal axis, the guiding structure also permitting the turntable base to translate along the vertical axis, the guiding structure preventing the turntable base from substantial translational movement in the horizontal plane and substantial rotational movement about either the vertical axis or an axis orthogonal to both the horizontal and vertical axes; and at least two electric motors, with each of the electric motors applying force to the turntable base along the vertical axis in at least two distinct areas of the turntable base, the two areas residing on opposite sides of the horizontal axis, the electric motors being capable of translating the turntable base along the vertical axis and pivoting the turntable base about the horizontal axis, the printed circuit board thus residing in a predetermined vertical location and rotational orientation about the horizontal and vertical axes.

43. The adjusting mechanism of claim 42, wherein the mechanical guiding structure comprises:

at least two vertical shafts rigidly attached at the bottom end to a stable base;

a coupling plate defining a hole for each vertical shaft, the shafts protruding through the holes so that the coupling plate is held in a substantially horizontal fashion while being allowed to translate vertically;

a pivot joint coupling the coupling plate with the turntable base, the pivot joint permitting the turntable base to pivot about the horizontal axis.

44. The adjusting mechanism of claim 43, wherein the stable base is a horizontal translation table capable of translating the adjusting mechanism horizontally.

45. The adjusting mechanism of claim 42, wherein the electric motors are servo motors.

46. The adjusting mechanism of claim 42, wherein the electric motors are stepper motors.

47. The adjusting mechanism of claim 42, further comprising at least one spring compressed between a stable base and the mechanical guiding structure to reduce the force required by the electric motors to translate the turntable base upward along the vertical axis.

48. The adjusting mechanism of claim 42, further comprising at least one counterweight assembly applying force upward against the mechanical guiding structure to reduce the force required by the electric motors to translate the turntable base upward along the vertical axis.

49. An x-ray laminography inspection system for inspecting a printed circuit board, comprising:
- the adjustment mechanism of claim 42, the adjustment mechanism holding the printed circuit board;
- a horizontal translation table attached to the adjustment mechanism;
- an algorithmic controller that controls the movement of the adjustment mechanism and the horizontal translation table;
- an x-ray source located near one side of the printed circuit board; and
- an x-ray detector, the printed circuit board located between the x-ray source and the x-ray detector, the adjustment mechanism and the horizontal translation table positioning and orienting the printed circuit board so that an area of the printed circuit board being inspected lies substantially within the depth of focus of a focal plane located between and defined by the location of the x-ray source and the x-ray detector.

50. A method for adjusting both the location of an object along a vertical axis and the rotational orientation of the object about a first and second horizontal axes, the first and second horizontal axes each being orthogonal to the vertical axis and to each other, the method comprising the steps of:
- guiding the motion of the object by permitting the object to pivot about the first and second horizontal axes and to translate along the vertical axis, while preventing the object from substantial horizontal translational movement and substantial rotational movement about the vertical axis; and
- translating at least three distinct areas of the object substantially along the vertical axis, the three areas being positioned so that the object may also be rotated about the first and second horizontal axes, so that the object resides in a predetermined vertical location and rotational orientation about the horizontal axes.

51. A method for adjusting both the location of an object along a vertical axis and the rotational orientation of the object about the vertical axis and a horizontal axis that is orthogonal to the vertical axis, the method comprising the steps of:
- guiding the motion of the object by permitting the object to pivot about the horizontal axis, to rotate about the vertical axis, and to translate along the vertical axis, while preventing the object from substantial translational movement in the horizontal plane and substantial rotational movement about an axis orthogonal to both the horizontal and vertical axes;
- rotating the object about the vertical axis; and
- translating at least two distinct areas of the object along the vertical axis, the two areas residing on opposite sides of the horizontal axis, so that the rotating and translating steps cause the object to reside in a predetermined vertical location and rotational orientation about the vertical and horizontal axes.

* * * * *